United States Patent [19]

Gago et al.

[11] Patent Number: 4,661,351

[45] Date of Patent: Apr. 28, 1987

[54] COMPOSITIONS CONTAINING BIOSYNTHETIC PESTICIDAL PRODUCTS AND AT LEAST ONE PHOSPHATE, PROCESSES FOR THEIR PREPARATION AND THEIR USE

[75] Inventors: Ignace Gago, Braine-l'Alleud; René Detroz, Ohain, both of Belgium

[73] Assignee: Solvay & Cie, Brussels, Belgium

[21] Appl. No.: 605,939

[22] Filed: May 1, 1984

[30] Foreign Application Priority Data

May 2, 1983 [FR] France .................................. 83 07399

[51] Int. Cl.$^4$ ............................................ A01N 63/02
[52] U.S. Cl. ........................................ 424/93; 435/253;
435/822; 435/832; 71/3; 71/4; 424/DIG. 8
[58] Field of Search ............................ 424/93, DIG. 8;
435/253, 822, 832; 260/112 R; 71/3, 4

[56] References Cited

U.S. PATENT DOCUMENTS

| | | | |
|---|---|---|---|
| 3,087,865 | 4/1963 | Drake et al. | 195/96 |
| 3,150,062 | 9/1964 | Greenberg et al. | 195/96 |
| 4,325,937 | 4/1982 | Spence et al. | 424/88 |

FOREIGN PATENT DOCUMENTS

| | | | |
|---|---|---|---|
| 2449401 | of 0000 | France . | |
| 0000155 | 4/1979 | PCT Int'l Appl. | 424/93 |
| 1172900 | 12/1969 | United Kingdom . | |
| 2093860 | 9/1982 | United Kingdom | 435/172.1 |

OTHER PUBLICATIONS

*Chemical Abstracts,* vol. 90, No. 24, Jun. 11, 1979, p. 109, No. 188844p.

*Primary Examiner*—John Kight
*Assistant Examiner*—Garnette D. Draper
*Attorney, Agent, or Firm*—Spencer & Frank

[57] ABSTRACT

The compositions contain biosynthetic pesticidal products originating from microorganisms of the family of Bacillaceae and at least one water-soluble inorganic phosphate.

They can be used, if appropriate after dispersion in a liquid, for spraying.

**13 Cla

COMPOSITIONS CONTAINING BIOSYNTHETIC PESTICIDAL PRODUCTS AND AT LEAST ONE PHOSPHATE, PROCESSES FOR THEIR PREPARATION AND THEIR USE

The present invention relates to compositions containing biosynthetic pesticidal products originating from microorganisms of the family of Bacillaceae, and to processes for their preparation and their use.

Biosynthetic pesticidal products have several advantages over chemical pesticides, in particular because of their high specificity. Thus, biosynthetic pesticides which are toxic or pathogenic to insects are in general non-toxic and non-pathogenic to humans and other living beings. In addition, considering their specificity, they do not in general endanger either the predators and natural parasites of the insects it is desired to eliminate or beneficial insects. They are not phytotoxic and do not leave any toxic residue. Finally, the insects do not appear to develop resistance to this type of pesticide, in contrast to the effect of the use of organic insecticides obtained by synthesis.

Biosynthetic pesticides can be obtained from very diverse microorganisms. One class of biosynthetic pesticide most commonly used in combating certain insects is obtained from *Bacillus thuringiensis,* of which numerous species are known.

Since biosynthetic pesticides are in general insoluble, particular techniques are necessary for their application. They may be in the form of dry solid particles or in the form of suspensions of solid particles in an appropriate liquid. In general, they are used in the form of suspensions, which are sprayed onto the infested zones by various techniques which are known per se. One technique which is frequently used to treat large areas, such as forests or wide expanses of cultivated land or even wide expanses of water, marshland or rivers consists in aerial spraying of suspensions of biosynthetic pesticides.

U.S. Pat. No. 3,087,865 (ROHM & HAAS Co.) has proposed the preparation of a biosynthetic pesticidal composition which contains spores, enveloping substances (crystals) and soluble toxins originating from micro-organisms of the genus Bacillus, such as *Bacillus thuringiensis*. These compositions can be in the form of suspensions or dry powders and can contain various additives. It is thus possible to use the powder obtained by drying the filter-cake of the fermentation product (powder), optionally dispersed in water (cream), or a concentrate of the fermentation medium (paste). Since the concentrated suspensions are viscous, it is essential to dilute them to a high degree in order to enable the product to be used correctly. When sprayed on, the suspensions therefore have a quite low concentration of active substances. The expanses which can be treated aerially in a single flight are therefore reduced. In addition, the suspensions frequently settle during storage.

The object of the present invention is to provide compositions which contain biosynthetic pesticidal products and do not have the disadvantages of known compositions. The object is to provide compositions of biosynthetic pesticidal products which are stable and keep their good activity during storage, and which have a high concentration of active substances such that the volume to be transported for a given dose of active substance is low. These compositions give concentrated suspensions which are fluid and stable, have a sufficiently low viscosity to enable them to be sprayed easily, do not have a tendency to settle, are easy to disperse, dilute or emulsify in diluents, such as gas oil and water, if dilution proves to be essential, without flocculation or settling phenomena being observed and without particular stirring being required, and which adhere well on the plants in a manner such that they are able to exert all of their activity, are highly resistant to low temperatures and, finally, do not pollute the environment. The compositions containing biosynthetic pesticidal products according to the invention give concentrated suspensions which are particularly suitable for aerial application and which can be used as such without additional dispersion in gas oil. The organic pesticidal substances in these suspensions do not coagulate.

The invention relates to compositions containing biosynthetic pesticidal products originating from microorganisms of the family of Bacillaceae and at least one water-soluble inorganic phosphate.

Water-soluble inorganic phosphate according to the invention is understood as meaning inorganic phosphates which are added to biosynthetic pesticides or to their precursors at any stage of their preparation or of the preparation of the compositions according to the invention as long as this is after the fermentation of the micro-organisms generating them, and of which the solubility in water is at least 5 g/liter, preferably at least 10 g/liter.

Various water-soluble inorganic phosphates can be present in the compositions according to the invention. In general, phosphates chosen from acid phosphates and condensed phosphates are preferred.

Acid phosphates are understood as meaning derivatives of phosphoric acids corresponding to the formula $$H-O-\left[\begin{array}{c} O \\ \parallel \\ P-O \\ | \\ O \\ | \\ H \end{array}\right]_n -H$$

where $n=1$ to 3, that is to say ortho-, pyro- and tripolyphosphoric acids which are only partly salified. These can be used as such, in the form of partly salified phosphoric acids, such as mono-H or di-H orthophosphates. They can also be used in the form of mixtures of completely salified phosphates corresponding to the acids. In this case, inorganic or organic acids, such as phosphoric acid, citric acid or ascorbic acid, can be used. Mixtures of sodium tripolyphosphate and citric acid can thus be used.

Condensed phosphate is understood as meaning all phosphates which have a cyclic structure, also called metaphosphates or polymetaphosphates, polyphosphates with long linear chains containing at least 4 phosphorus atoms in their molecule and all branched-chain polyphosphates, including polyphosphates with chains containing rings in their structure, which are sometimes called ultraphosphates. These condensed phosphates have several sequences of phosphorus-oxygen bonds in their molecule. Advantageous cyclic phosphates are the trimetaphosphates, the tetrametaphosphates and the hexametaphosphates. Of these, the hexametaphosphates are particularly suitable. Suitable polyphosphates are in general those which contain on average less than 100 phosphorus atoms, most frequently less than 50 phosphorus atoms, in their molecule. Of these, the polyphosphates containing on average at least 6 phosphorus atoms in their molecule are particularly suitable. Good results have been obtained with vitreous polyphosphates.

The phosphates according to the invention are in general in the form of alkali metal, alkaline earth metal or ammonium salts. Good results have been obtained with phosphates of sodium, potassium or ammonium. The best results have been obtained with phosphates of sodium.

Mixtures of phosphates such as those defined above may also be suitable.

In general, a phosphate, a mixture of various phosphates or a mixture of phosphates and acids which is capable of conferring to water an approximately neutral or slightly acid pH is chosen. In general, phosphates or mixtures based on phosphates which are capable of conferring to water a pH not exceeding 7 are chosen. Phosphates or mixtures based on phosphates such that aqueous solutions containing 10 to 300 g/liter of these phosphates have a pH not exceeding 6 are preferably chosen. The phosphates or mixtures of phosphates are most frequently chosen so that such aqueous solutions have a pH of at least 3, advantageously at least 3.5 and preferably at least 4.

Although all the phosphates defined above are suitable, commercially available condensed phosphates in which the $Na_2O:P_2O_5$ ratio is about 1:1 to 1.2:1, such as sodium hexametaphosphate, and mixtures of vitreous polyphosphates referred to as Graham salts, which are also called sodium hexametaphosphate, are preferred.

The phosphates are present in various amounts in the compositions according to the invention. In general, their amount by weight is at least 0.01 times, preferably at least 0.03 times and most frequently at least 0.1 times, that of the dry biosynthetic pesticidal products. In general, their amount by weight does not exceed 5 times, preferably 3 times and most frequently twice, the dry weight of the biosynthetic pesticides.

Biosynthetic pesticidal products according to the invention are understood as meaning biosynthetic pesticidal products which originate from microorganisms of the family of Bacillaceae and which can be used to combat animal and plant parasites of humans, animals and plants (excluding microorganisms which cause diseases in humans and animals) and vectors of parasitic and viral diseases. These biosynthetic pesticides can thus have a fungistatic or fungicidal action, also called an anticryptogamic action, a herbicidal action or an action against arthropods, and more particularly against insects. The invention particularly applies to biosynthetic pesticides which originate from microorganisms of the family of Bacillaceae and which have an insecticidal action.

The biosynthetic pesticides contained in the compositions according to the invention preferably originate from microorganisms of the genus Bacillus. Particularly suitable pesticides of this type are the biosynthetic pesticides derived from microorganisms such as *Bacillus thuringiensis, Bacillus sphaericus, Bacillus popilliae, Bacillus cereus, Bacillus lentimorbus* and *Bacillus fribourgensis.*

Good results have been obtained with all serotypes of *Bacillus thuringiensis,* and more particularly with those of serotypes 1, 3a, 3a3b, 7, 9, 10 and 14. The best results have been obtained with *Bacillus thuringiensis* of serotype 1 (*thuringiensis* species), 3a3b (*kurstaki* species), 7 (*aizawa* species) and 14 (*israelensis* species).

The biosynthetic pesticides contained in the compositions according to the invention can also originate from any microorganisms transformed by insertion of DNA which codes the production of toxins and which originates from pathogenic microorganisms of the family of Bacillaceae.

The biosynthetic pesticides can be in very diverse forms in the compositions according to the invention. Thus, they can be in the form of the organisms themselves, at any stage of their development, including possible vegetative forms, as such, together with their culture medium, in the completely or partly lysed form, in the completely or partly sporulated form, in a form in which spores have been partly or completely released by various means, such as bacterial autolysis, in the form of products which are excreted spontaneously by the organisms, such as exotoxins, in the form of products which can be extracted from these organisms, such as endotoxins, by any known method which in itself may or may not involve lysis of the organism in question, in the form of products which may be released from the organisms in the course of certain stages of their development (crystals which may or may not be associated with the spores) or in several of these forms simultaneously.

If appropriate, these various forms may be associated with residues of culture medium. Good results have been obtained with the mixture containing spores, associated crystals and, where relevant, exotoxins which are formed spontaneously during autolysis of the bacteria at the end of sporulation. In addition to the spores, the crystals which may or may not be associated with the spores and, where relevant, the exotoxins, such a mixture may contain cells or cell debris as well as residual solid products from the nutrient medium used during culture.

The compositions according to the invention may also contain several biosynthetic pesticides of various origins.

The compositions according to the invention may furthermore contain various other additives. They may contain perfumes or odour masks, and various preservatives, such as antioxidants, antibacterial agents (bactericidal or bacteriostatic agents), agents which are capable of absorbing ultraviolet radiation (which may possibly cause deactivation of the biosynthetic pesticide), fillers and agents which regulate the pH. They may also contain organic pesticides obtained by synthesis (chemical pesticides).

Finally, the compositions according to the invention may contain other additives, the nature and function of which depend on the intended use. Thus, if the composition is to be sprayed, if appropriate after dispersion in an appropriate liquid, onto the surfaces of plants, it may contain adhesives, tackifying agents or wetting agents such that the adhesion of the composition is increased. The wetting agents can be any type of hydrophilic product, in particular products chosen from polyhydroxylated products, such as glycerol, saccharides or ethylene glycol, and surface-active agents. These can be hydrophilic surface-active agents or surface-active agent mixtures containing a hydrophilic surface-active agent. Particularly suitable hydrophilic surface-active agents are those which have a hydrophilic-lipophilic balance (HLB), as defined by P. Blonchard (Parf. Cosm.

Sav., 1969, 12 (2), February, pages 82 to 91), of at least 9, and most frequently of at least 10.

If the compositions according to the invention are dispersed or are intended to be dispersed in a liquid, additives which are soluble or dispersible in the solvent constituting the liquid phase are most frequently chosen. In general, additives which are water-soluble are chosen.

The various additives are in general present in amounts which do not exceed the amount by weight of the biosynthetic pesticides. They are most frequently present in amounts of 1 to 100% by weight of the weight of the biosynthetic pesticides. The content of wetting agents in general does not exceed the weight, and preferably does not exceed 0.8 times the weight, of the biosynthetic pesticides. The wetting agents are most frequently present in an amount of 1 to 75% by weight of the biosynthetic pesticides.

Finally, the compositions according to the invention may also contain residues from the preparation of the biosynthetic pesticide.

The compositions according to the invention may be in the form of dry powders or in the form of suspensions in a liquid.

The compositions in the form of dry powders contain a biosynthetic pesticide in the form of a dry powder, a phosphate according to the invention and, if appropriate, other additives. The biosynthetic pesticide used, in the form of a dry powder, may contain small amounts of water. In the case of *Bacillus thuringiensis*, the biosynthetic pesticide in general comprises spores, associated crystals and, if appropriate, exotoxins and in general contains, after drying, less than 15% by weight of water, usually less than 12% of water. It most frequently contains 2 to 10% of water.

The content of biosynthetic pesticides in the compositions in the form of powders is in general 20 to 98%, and most frequently 30 to 90%, of the weight of the composition, and that of the condensed phosphates is in general 2 to 80%, most frequently 10 to 70%, of the weight of the composition. These compositions may also contain 0 to 50%, and most frequently 0.1 to 30%, by weight of various additives.

The content of biosynthetic pesticides in the compositions in the form of powders is in general 20 to 90%, and most frequently 30 to 85%, of the weight of the composition, and that of the acid phosphates is in general 10 to 80%, and most frequently 15 to 70%. In the case where the composition contains acid phosphates, minimum amounts of the order of 10% of these phosphates and/or the presence of wetting agents, such as glycerol, have proved essential.

The compositions according to the invention in the form of dry powders in general contain a phosphate or a mixture based on a naturally occurring phosphate in amounts such that, if they are mixed with at least the equivalent of their weight of water, they confer a pH which does not exceed 7, and preferably does not exceed 6. In general, care is taken that the pH of the suspensions thus obtained is not less than 3.0, preferably not less than 3.5.

If the compositions according to the invention are in the form of suspensions, they also contain a solvent. The latter should be inert towards the biosynthetic pesticides and, in particular, should not deactivate them. The solvent can consist of a single solvent or a mixture of solvents. The solvents chosen are most frequently those which dissolve the phosphates. In general, the solvent contains water. Good results have been obtained when the solvent contains at least 60%, preferably at least 80%, by weight of water.

The compositions according to the invention are advantageously in the form of a suspension of solid particles of the biosynthetic pesticides in a liquid containing the solvent, the phosphates and any additives. These concentrated suspensions in general contain 3 to 40% by weight, most frequently 5 to 30% by weight, of biosynthetic pesticides and 60 to 97% by weight, most frequently 70 to 95% by weight, of liquid. The liquid may contain 60 to 99% by weight of solvent and an amount of phosphates in general not exceeding 50%, preferably 40%, of the weight of liquid, and most frequently an amount greater than 1%, preferably greater than 3%, of the weight of the liquid. If appropriate, the liquid may contain 0.01 to 60% by weight, most frequently 0.1 to 40% by weight, of other additives.

The compositions according to the invention in the form of suspensions are thixotropic such that their viscosity greatly depends on the stirring to which they have been subjected.

The compositions according to the invention in the form of suspensions in a liquid containing water have a pH which in general does not exceed 7, and preferably does not exceed 6. In general, their pH is greater than 3, preferably than 3.5.

The present invention also relates to processes for the preparation of the compositions according to the invention.

The phosphates according to the invention are used to form the compositions according to the invention at any stage of the preparation of the biosynthetic pesticides or, if appropriate, their precursors or of the preparation of the compositions according to the invention, as long as this is after the fermentation of the microorganisms which generate the said pesticides.

A suitable process for the preparation of compositions according to the invention comprises taking the culture medium of the microorganisms which generate the biosynthetic pesticidal products, and separating off the water by conventional techniques for separating off water, such as centrifugation, ultrafiltration, precipitation by addition of a non-solvent, such as acetone, or flocculation, such that a paste is obtained.

In the case of *Bacillus thuringiensis,* the culture medium is taken, for example, at the end of the sporulation phase.

Another process comprises separating off, at the end of the sporulation phase, the fractions rich in crystals or in spores or in these two products together from the culture medium of the microorganisms which generate the biosynthetic pesticidal products. These fractions are then treated by the same techniques as those used for the treatment of the pastes.

To obtain compositions in the form of dry powders, the paste thus obtained is dried by conventional techniques, such as drying by atomisation, drying by lyophilisation or drum-drying such that solid particles containing in general less than 15%, preferably less than 12%, of water are obtained. The solid particles of pesticide are mixed with the phosphate according to the invention in solid form and with any other additives. An advantageous technique comprises incorporating the phosphate and any other additives in the course of pulverisation of the solid particles of pesticide.

Another technique comprises adding the phosphate and any other additives to the paste before drying it, and subjecting the mixture to drying according to one or other of the techniques indicated above.

To obtain the compositions according to the invention in the form of suspensions, the solid particles of pesticide can be dispersed in a liquid phase, which preferably contains water and contains, in addition, the phosphate and any other additives, to form a cream.

Another technique comprises incorporating the phosphates, if appropriate in the form of a concentrated solution, and any other additives into the paste obtained after removal of the water from the fermentation medium.

The present invention also relates to a process for using the compositions.

The compositions according to the invention can be used as pesticides, and more particularly as agents for eliminating insects at any stage of their development. For this purpose, they are sprayed, onto the areas infested, by any methods which are known per se, such as manual spraying, mechanical spraying and, more particularly, aerial spraying. In particular, they can be sprayed onto areas infested by insects, and more particularly by Lepidoptera, Diptera, Coleoptera, Aphaniptera, Orthoptera, Isoptera and Homoptera.

The doses used are a function of the biosynthetic pesticide used and the pathogenic agent to be eliminated.

In the case of *Bacillus thuringiensis*, and more particularly of serotypes 1, 3a3b, 7 and 14, in general 50 to 5,000 g of solid particles are sprayed per hectare. The compositions according to the invention can be sprayed as such, if they are in the form of suspensions. They can also be dispersed, diluted or emulsified in a diluent, such as water or an organic diluent, such as a product of the distillation of petroleum (for example gas oil). In this case, they are diluted by 1 to 300 times, preferably 4 to 120 times, their volume of diluent.

Examples of compositions according to the invention (Examples 2 to 8) and of a comparison composition (Example 1) are given below in order to illustrate the invention.

EXAMPLE 1

The mixture obtained during the fermentation of *Bacillus thuringiensis* serotype 3a3b (*kurstaki* species) (B.t.3) is centrifuged, after sporulation, to give a paste containing about 10 to 12% of solids. The paste is dried by atomisation.

The primary powder thus obtained has an activity of 80,000 international units (IU) per mg, measured with the aid of *Anagasta kuhniella* Z. in accordance with the biological titration method of L. Charmoille et al. (Phytiatrie-Phytopharmacie, 1974, 23, pages 223-234).

When 40 g of the primary powder are mixed with 210 g of water, neither a paste nor a suspension can be formed. The mixture, called product 1, is heterogeneous and contains the dry powder and large agglomerates of moist powder.

EXAMPLES 2 TO 7

The same primary powder as that used in Example 1 was used to prepare 6 different compositions, called products 2 to 7.

40 g of this powder are suspended in a liquid mixture containing various additives. The nature and amounts of the additives are shown in Table I below.

The viscosity of the suspensions obtained was measured with the aid of a Brookfield RVT viscometer at a speed of 10 revolutions per minute.

The dispersibility of the suspension in water was measured by the following technique. 5 cm$^3$ of suspension are poured into 250 ml of water in a stemmed glass. If the product disperses instantly, the dispersibility is judged perfect (PFT). If the product disperses completely after one revolution of the stemmed glass, the dispersibility is judged very good (VG). After 2 revolutions of the stemmed glass, it is judged good (G). If it is necessary to subject the stemmed glass to more than two revolutions to disperse the product, the dispersibility is judged insufficient (I).

The results of these evaluations and the pH of the suspensions are shown in Table I below.

TABLE I

| PRODUCT | 2 | 3 | 4 | 5 | 6 | 7 |
|---|---|---|---|---|---|---|
| Composition, % | | | | | | |
| primary powder of B.t.3a3b | 16 | 16 | 16 | 16 | 16 | 16 |
| Na hexametaphosphate | 15 | 15 | 2 | | | |
| NaH$_2$PO$_4$ | | | | 15 | | |
| Na$_3$PO$_4$.12H$_2$O | | | | | 10 | |
| Na tripolyphosphate | | | | | | 3 |
| glycerol | | 10 | 10 | 10 | | |
| water | 69 | 59 | 72 | 59 | 74 | 81 |
| Properties | | | | | | |
| pH | 5.4 | 5.5 | 5.8 | 4.1 | 12.6 | 8.5 |
| viscosity, mPa.s | 430 | 300 | 820 | 580 | 5800 | 5500 |
| dispersibility | PFT | PFT | G | VG | I(10)* | I(4)* |

*number of revolutions necessary to obtain complete dispersion.

EXAMPLE 8

The mixture obtained during the fermentation of *Bacillus thuringiensis* serotype 14 (B.t.14) is centrifuged, after sporulation, to give a paste, which is dried by atomisation.

The primary powder thus obtained has an activity of about 10,000 international units (IU) per mg, measured with the aid of *Aedes aegypti* by the biological titration method of H. de Barjac and I. Larget, WHO-VBC-79.744.

40 g of this powder are suspended in a liquid mixture containing 172.5 g of water and 37.5 g of sodium hexametaphosphate to form a composition called product 8.

The suspension thus obtained has a viscosity, measured by the technique indicated in Examples 2 to 7, of 490 mPa.s. Its dispersibility in water is very good (VG). Its activity is 2,800 IU per mg of suspension.

We claim:

1. Compositions containing biosynthetic pesticidal fermentation products of microorganisms of the family of Bacillaceae, comprising at least one water-soluble inorganic condensed acid phosate and a wetting agent, said compositions having a neutral or slightly acid pH in water.

2. Compositions according to claim 1, comprising at least one condensed phosphate selected from the group consisting of metaphosphates, polymetaphosphates, linear polyphosphates having at least 4 phosphorus atoms, branched chain polyphosphates, branched chain polyphosphates having rings in their structure, and mixtures thereof.

3. Compositions according to claim 1, comprising sodium hexametaphosphate.

4. Compositions according to claim 1, comprising glycerol.

5. Compositions according to claim 1, wherein said phosphates are present in amounts of 0.03 to 3 times the dry weight of the biosynthetic pesticides.

6. Compositions according to claim 1, characterised in that they are in the form of a suspension of of solid particles of the biosynthetic pesticidal products in an aqueous solution containing the phosphate.

7. Compositions according to claim 1, characterised in that they are in the form of a solid mixture of particles of the biosynthetic pesticidal products containing at least one phosphate in the solid state.

8. Process for the preparation of compositions containing biosynthetic pesticidal fermentation products of microorganisms of the family of Bacillaceae, comprising at least one water-soluble inorganic condensed acid phosphate and a wetting agent, said compositions having a neutral or slightly acid pH in water, comprising, fermenting microorganisms of the family Bacillaceae that produce biosynthetic pesticidal products in an aqueous medium to produce pesticidal products, removing water from the aqueous medium to produce a paste, drying said paste to form a dry material having a water content of less 15% by weight, and combining said material with said water-soluble inorganic condensed acid phosphate.

9. Method of eliminating insects from infested areas, comprising spraying compositions containing biosynthetic pesticidal fermentation products of microorganisms of the family of Bacillaceae, comprising at least one water-soluble inorganic condensed acid phosphate and a wetting agent, said compositions having a neutral or slightly acid pH in water, onto the infested areas.

10. The process of claim 8, wherein the dried paste material is dispersed in an aqueous solution containing the phosphate.

11. The process of claim 8, wherein the dried paste material is combined with at least one solid phosphate and pulverized.

12. The composition of claim 1, having a pH of from 3 to 7 in water.

13. The composition of claim 12, having a pH of from 4 to 6 in water.

* * * * *